(12) United States Patent
Sander

(10) Patent No.: US 7,518,791 B2
(45) Date of Patent: Apr. 14, 2009

(54) MICROSCOPE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 362 days.

(21) Appl. No.: 11/568,649

(22) PCT Filed: Apr. 7, 2005

(86) PCT No.: PCT/EP2005/003676

§ 371 (c)(1),
(2), (4) Date: Nov. 3, 2006

(87) PCT Pub. No.: WO2005/109068

PCT Pub. Date: Nov. 17, 2005

(65) Prior Publication Data

US 2007/0216998 A1    Sep. 20, 2007

(30) Foreign Application Priority Data

May 6, 2004   (DE) .................. 10 2004 022 330

(51) Int. Cl.
*G02B 21/00* (2006.01)
(52) U.S. Cl. ..................................... 359/368
(58) Field of Classification Search .......... 359/368–398
See application file for complete search history.

(56) References Cited

U.S. PATENT DOCUMENTS

| 5,526,812 | A | 6/1996 | Dumoulin et al. |
| 5,694,142 | A | 12/1997 | Dumoulin et al. |
| 6,038,467 | A | 3/2000 | De Bliek et al. |
| 6,525,878 | B1 | 2/2003 | Takahashi |
| 2004/0047044 | A1 | 3/2004 | Dalton |

*Primary Examiner*—Joshua L Pritchett
(74) *Attorney, Agent, or Firm*—Hodgson Russ LLP

(57) ABSTRACT

Microscope comprising microscope optics (25), a camera device (7) for recordal of images, captured by the microscope optics (25), of an object to be observed, and a display apparatus (12) which can be viewed by an observer for displaying the images taken by the camera device (7), wherein at least one area of the display apparatus (12) is constructed as a deflecting device (13) for deflecting light beams emitted by the object which is to be observed into the microscope optics (25).

11 Claims, 1 Drawing Sheet

MICROSCOPE

CROSS-REFERENCE TO RELATED APPLICATIONS

Figure 1:
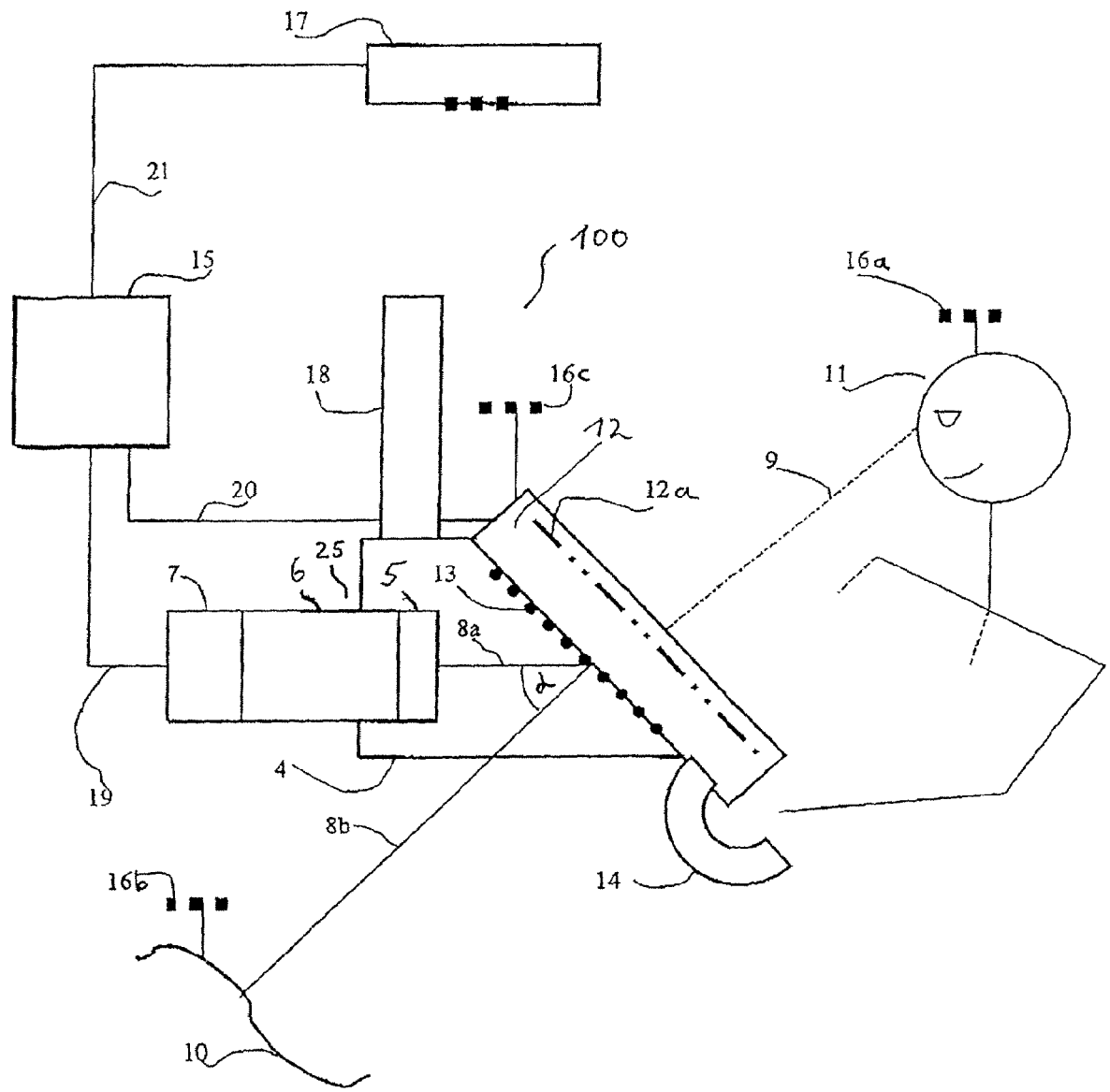

The present application is the U.S. National Stage of International Application No. PCT/EP2005/003676 filed Apr. 7, 2005, which claims priority of German Application No. 10 2004 022 330.0 filed May 6, 2004.

FIELD OF THE INVENTION

The present invention relates to a microscope of a type comprising microscope optics, a camera device for recordal of images captured by the microscope optics of an object to be observed, and a display apparatus which can be viewed by an observer for displaying the images recorded by the camera device.

BACKGROUND OF THE INVENTION

When using microscopes, e.g. operating microscopes, particularly in microsurgery, there has long been a need for the operator, particularly the surgeon or person performing the operation, not to have to look directly through the eyepieces of the microscope but to have a substantially unimpeded view of the operating area and at the same time to see an enlarged image of the operating area. It should be noted that such needs apply particularly also to stereomicroscopes, used in both medical and technical fields. Microscopes of this kind have hitherto been referred to as free-view microscopes.

The first steps in this direction were taken by the company Vision Engineering using the "Isis" microscope system. In this system the user does indeed look through two eyepieces, but the considerable distance of the eyes from the eyepieces and the large exit pupil allow him to move relatively freely in front of the eyepieces. A similar system produced by this company and marketed under the name "Mantis" is also known. In the latter the user looks at a large field of vision for both eyes through a common Fresnel plate.

Reference should also be made to developments in the field of graphic representation using displays which enable data and images to be made stereoscopically visible to an operator directly over an operating field. A system of this kind was exhibited by the Fraunhofer-Institut INK at the trade fair MedTech 2003 in Stuttgart. In it, a display screen can be positioned over an operating field by means of a support arm. The display screen is freely movable by hand. Its position in space is located by sensors and correlated with images displayed on the display screen, for example X-ray images. The observer can view these displayed images stereoscopically through stereospectacles and at the same time study the operating area through the partly transparent display screen. When the user changes the position of the display screen over the operating area, the viewed position of the correlated X-ray images also changes accordingly.

A system of this kind is described in EP 0918491 B1.

However, it is not possible to carry out microsurgery by the method described therein as only data and images obtained pre-operatively can be shown on a display.

SUMMARY OF THE INVENTION

The aim of the present invention is to provide a magnified view of an operating field, while allowing a user, especially a surgeon, to have a free view.

This objective is achieved by means of a microscope characterised in that at least one area of the microscope's display apparatus is constructed as a deflecting device for deflecting light beams emitted by the object which is to be observed into the microscope optics.

The microscope according to the invention is characterised by its ergonomically particularly favourable operation. The operator can easily study the operating area by viewing a screen or display without keeping his eyes directly on the eyepiece. Thanks to the alignment or deflection of the microscope axis according to the invention it is particularly easy to carry out an operation while at the same time observing the operating field on the display screen. The deflection according to the invention of light beams emitted from the object under observation, which takes place at the display device, enables the microscope optics to be positioned at a distance from the display device or from the object, as a result of which the display device can be positioned on the object in a particularly favourable manner so that the desired free operating distance can easily be selected.

Advantageous embodiments of the microscope according to the invention are the subject of the subsidiary claims.

Expediently, the side of the display device facing away from the observer (the reverse side) is at least partly constructed as a deflecting device for light beams emitted from the object which is to be observed. In this way it is possible to arrange the object which is to be observed substantially behind the display for the observer, as a result of which, for example, an operation to be carried out by the observer can be performed on the object under observation in an ergonomically favourable manner.

It is preferable if the area of the display apparatus constructed as a deflecting device is aligned such that the light beams emitted by the object under observation and deflected into the microscope optics extend substantially in the direction of a line of sight of the observer before being deflected. This special configuration ensures particularly natural handling of the microscope for the observer performing an operation on the object under observation, i.e. the line of sight from the eye of the observer through the display apparatus to the object under observation is substantially parallel to the line of sight which the observer would have if the display apparatus were not interposed.

It is particularly preferable to construct the display apparatus of the microscope according to the invention as a flat screen. A flat screen of this kind can be constructed in known manner as an LCD flat screen, for example. LCDs or liquid displays of this kind are characterised by their very low current consumption and a very flat design. Liquid displays typically do not generate any light themselves but are capable of reflecting or transmitting light hitting them. It is conceivable, for example, to construct both a display screen which can be viewed by the observer (on the front) and the deflecting device (on the back) of the display apparatus as an LCD screen. It is also possible to use OEL Systems (Organic Electroluminescence Systems) as the display screen and/or deflecting device. OEL systems are characterised in that they emit light independently, under the effect of current, and do not require any additional illumination.

According to a particularly preferred embodiment of the microscope according to the invention the display apparatus can be switched into transparent mode, in which the light beams emitted by the object under observation are at least partly transmitted. By this measure, the observer can if necessary be provided with a direct free view of the object under observation, without having to move or take away the display even for a short time. LCD or OEL screens can be switched into reflecting and into transmitting mode by suitable application of current or voltage. Reference is made in particular to polar or polarising layers (polarising films) which can be applied between corresponding transparent sheets or films. By arranging two such layers, also known as the polarising layer and analysing layer, one behind the other it is possible to provide a reflecting or transmitting screen by suitable individual application of current or voltage to the layers. Polarising layer systems of this kind are suitable within the scope of the present invention both as a (reverse-side) deflecting device, which can also be switched to transmitting mode, and as a display screen, which can also be switched to transmitting mode if necessary.

It has also proved convenient to construct the part of the display apparatus which is designed as the deflecting element to have a mirror finish. This provides a particularly simple and effective method of deflecting the light beams emitted by the object under observation, in accordance with the invention.

According to a preferred embodiment of the microscope according to the invention, the area of the display apparatus constructed as a deflecting device is in the form of an electronically switchable mirror. Such a mirror may comprise, in particular, a plurality of small, individually adjustable or pivotable mirrors (micromirror array). In this way, by suitable angular positioning of the individual mirrors, it is easily possible to achieve both suitable deflection of the light beams emitted by the object under observation into the optics of the microscope, and the transparent mode mentioned above. It is also possible to construct the area of the display apparatus which is designed as a deflecting device with a sheet of glass or other suitable means which is or are constructed to be partly reflective. When using a sheet of glass of this kind as a deflecting device it would be possible to achieve the transparent mode simply by switching the display screen 12a to transmitting mode.

According to another preferred embodiment of the microscope according to the invention it is also possible to construct the area of the display apparatus designed as a deflecting device in the form of a switchable and/or holographically reflective display. This opens up the possibility of projecting markings and image data (such as the outlines of tumours) directly on the object under observation, using a laser which is to be arranged parallel to the microscope or to the microscope optics.

Particularly advantageously, the microscope according to the invention is constructed as a stereomicroscope. Operations can be carried out particularly advantageously using a stereomicroscope of this kind.

It is also preferable to construct the display apparatus with a stereoscopic viewing function. This also includes the possibility of observing the display apparatus, particularly a corresponding LCD or OEL screen, with polarising spectacles, thus enabling the images shown on the screen to be viewed stereoscopically. It is also conceivable to use the screen or the display in an autostereoscopic version, thus doing away with the need for the observer to wear polarising spectacles.

According to another preferred embodiment of the microscope according to the invention, it has a function such that external data can be displayed spatially stereoscopically and with true magnification, according to a selected magnification of the microscope optics. With this function it is possible to superimpose external data or images on a microscope image in a particularly simple and favourable way.

BRIEF DESCRIPTION OF THE DRAWING FIGURES

A preferred embodiment of the invention will now be described in more detail with reference to the accompanying drawings, where:

FIG. 1 shows a schematic side view of a preferred embodiment of the microscope according to the invention.

DETAILED DESCRIPTION OF THE INVENTION

A microscope according to the invention is generally designated 100 in FIG. 1. The microscope 100 is used by an observer 11 for viewing an object 10. The object 10 may, in particular, be an operating area which is to be operated on by the observer 11.

The microscope 100 has a microscope housing 4 comprising an objective 5 and a zoom device 6. The objective 5 and zoom device 6 are hereinafter also referred to collectively as the microscope optics 25. In addition, the microscope comprises an image recording or camera device 7 which may be provided inside or outside the microscope housing 4. The camera device 7 serves to record images of the object 10 under observation captured by the microscope optics 25.

Images captured by the camera device 7 are displayed to the observer 11 on a display screen 12a of a display apparatus 12 in the form of a flat screen. The display screen 12a is provided on the side of the display apparatus 12 facing the observer 11 (the front side). On the side of the display apparatus 12 facing away from the observer 11 (the reverse side) is a deflecting device constructed as a mirror surface 13.

Light beams emitted by the object 10 under observation along a first axis 8b are deflected on the mirror surface 13, to pass along an optical axis 8a of the microscope optics 25 and reach the objective 5 or the zoom device 6.

An angle α as shown in FIG. 1 can be achieved for example by using an array of micromirrors in which the individual mirrors or micromirrors have been brought into a corresponding pivoted position.

After suitable magnification by means of the objective 5 and the zoom device 6 and capturing by the camera device 7 the images taken are fed through an electronic connection 19 to a data processing unit 15. After suitable processing the images obtained from the data processing unit 15 are sent through another electronic connection 20 to the display screen 12a of the display apparatus 12. The observer views the display screen 12a along a line of sight 9 which typically extends substantially perpendicularly to the position of the display screen 12a. Of course, if suitable display screens are used, it is also possible to view the display screen 12a diagonally or at an angle.

As can be seen from FIG. 1, in a first approximation the direction of extent of the first axis 8b corresponds to the line of sight 9 of the observer. This ensures a very realistic observation by the viewer of the object 10 under observation, as the viewing axis 8b, 9 obtained overall corresponds substantially to the viewing axis which would be obtained if the display apparatus 12 were pivoted away or not there at all.

Conveniently, the microscope is designed so that it can produce stereoscopic images in known manner, while, in explanation of the representation in FIG. 1, it should be pointed out that two separate stereoscopic channels are located one behind the other in the plane of the drawing of FIG. 1 and therefore cannot be shown individually. The two stereoscopic images are converted into electronic signals by the camera device 7 (generally two CCDs) and are displayed stereoscopically on the display screen 12a through the data processing unit 15. According to a first embodiment it is possible, for example, for the observer 11 to wear polarising spectacles enabling him to view images shown on the display screen 12a stereoscopically. According to another possible embodiment the display apparatus 12 is used in an autostereoscopic version, which means that the viewer does not have to wear polarising spectacles. It is possible, for example, to provide spatial markings 16a on the observer's head to control the autostereoscopic system.

The image shown or the detail of the image of the object 10 shown can be magnified or reduced using the zoom device 6, again in a manner known per se, while the zoom device 6 may, for example, also be controlled by the viewer 11 manually, verbally or through a so-called eye control system. For this purpose control systems which can be actuated by the eye control system may be provided on the display screen 12a. These include for example functions which alter passive and active properties of the microscope, e.g. the zooming and/or focusing properties.

It is also possible to provide operating elements of the microscope on a handle 14, for example, or as a touch panel on the display apparatus 12.

For reasons of hygiene it is possible to design the display apparatus 12 or the microscope 100 as a whole so as to be bactericidal. Alternatively it is possible to enclose the microscope 100 at least partly in sterile film or transparent coverings or capsules (drapes).

In order to display, in addition to the microscope images, external images correlated with the operating area on the object 10, e.g. Computer Tomography or CT images, for example, spatial markings 16b, 16c are provided on the object 10 and microscope 100, the position of which can be located using one or more sensors or spatial sensors 17. Using suitable data processing, e.g. again the data processing unit 15, via an electronic connection 21, the exact position of the CT with respect to the object 12 can be displayed on the display screen 12a correlated with the selected or set magnification of the microscope in the true spatial position.

The microscope 100 according to the invention advantageously has a carrier system 18 constructed as a floor-, ceiling- or wall-mounted stand which is freely movable in space. The handle 14 mentioned earlier is used to manipulate the microscope in order to carry out such a movement and position it relative to the object 10.

It is also possible to move the microscope 100 in space by means of a so-called head control. The relative position of the head of the observer 11 to the microscope 100 is measured by means of the sensors 17 and spatial markings 16a, 16c, and suitable alterations are made on the carrier system 18 which bring the microscope 100 into a new desired position.

In order to give the observer 11 a free view directly of the object 10, if necessary (without going through the microscope optics 25) it is possible to switch the display apparatus 12 to transparent mode. For this, both the reverse side provided with the mirror surface 13 and the front side of the display apparatus 12 constructed with the display screen 12a are switched to a transmitting state.

For this purpose the mirror surface 13 may also be constructed as an electronically switchable mirror surface. For example, the mirror surface 13 may comprise a plurality of micromirrors arranged side by side, which can be pivoted to enable transmission. The angle of deflection α can also be chosen freely in suitable manner with this pivotable arrangement of a plurality of small mirrors (micromirror array).

It should also be pointed out once again that the position of the microscope optics 25 or of the microscope housing 4 relative to the display apparatus 12 is shown purely by way of example. If corresponding additional deflecting elements are used the axis 8a, 8b may also run differently.

It has proved particularly advantageous that in the microscope according to the invention the microscope optics 25 are not in the area between the display apparatus 12 and the object 10 under observation. As a result the display apparatus 12 can usefully be brought closer to the object 10 (shortening the length of the axis 8b), thus possibly making it easier for the observer 11 to carry out an operation on the object 10 by selecting a suitable free working distance.

The microscope 100 may if necessary also comprise an autofocusing system so that the observer does not have to manually refocus the microscope when a spatial adjustment is made.

FIG. 1 does not show any illuminating device; this may take different forms depending on the operating technique, for example it may run axially through the objective 5 or be in the form of an external annular or slot type illumination. It is also advantageously possible to construct the reverse side of the display apparatus 12 with white light or coloured light emitting diodes or LEDs for illuminating the object 10.

Finally it should be pointed out that the mirror surface 13 may be in the form of a switchable and/or holographic reflective display (e.g. an LCOS display). This makes it possible to project markings and image data, particularly the outlines of tumours, directly on the object by means of a laser arranged parallel to the axis 8a of the microscope.

List of Reference Numerals
- 4 Housing
- 5 Objective
- 6 Zoom device
- 7 Camera device
- 8a Microscope axis
- 8b First axis
- 9 Line of sight
- 10 Object
- 11 Observer
- 12 Display apparatus
- 12a Display screen
- 13 Mirror/deflecting device
- 14 Handle
- 15 Data processing unit
- 16a,b,c Spatial markings
- 17 Spatial sensors
- 18 Carrier system
- 19 Electronic connection
- 20 Electronic connection
- 21 Electronic connection
- 25 Microscope optics
- 100 Microscope
- α Angle of deflection

What is claimed is:

1. A microscope comprising:
   microscope optics for imaging an object;
   a camera device arranged to record images captured by the microscope optics; and
   a display apparatus connected to the camera device for displaying images recorded by the camera device to an observer, wherein at least one area of the display apparatus includes a deflecting device for deflecting light beams coming from an object into the microscope optics.

2. The microscope according to claim 1, wherein the deflecting device is provided on a side of the display apparatus opposite from a side of the display apparatus viewed by an observer.

3. The microscope according to claim 2, wherein the deflecting device is aligned so that the light beams coming from an object and deflected into the microscope optics extend substantially along a line of sight of an observer before the light beams are deflected by the deflecting device into the microscope optics.

4. The microscope according to claim 1, wherein the display apparatus includes a flat screen.

5. The microscope according to claim 1, wherein the display apparatus can be switched into a transparent mode in which the light beams coming from an object are at least partially transmitted through the display apparatus to an observer.

6. The microscope according to claim 1, wherein the deflecting device includes a mirror surface.

7. The microscope according to claim 1, wherein the deflecting device includes an electronically switchable mirror.

8. The microscope according to claim 1, wherein the deflecting device includes a switchable and/or holographic reflective display.

9. The microscope according to claim 1, wherein the microscope is a stereomicroscope.

10. The microscope according to claim 9, wherein the display apparatus (12) has a stereoscopic viewing function.

11. The microscope according to claim 10, further comprising spatial sensors for reading spatial markings on an object, whereby external data can be displayed stereoscopically, spatially and with the correct magnification by the display apparatus according to a selected magnification of the microscope optics.

* * * * *